(12) United States Patent
Schilling et al.

(10) Patent No.: US 11,576,802 B2
(45) Date of Patent: Feb. 14, 2023

(54) LOCKING HINGE

(71) Applicant: OTTO BOCK HEALTHCARE GMBH, Duderstadt (DE)

(72) Inventors: Matthias Schilling, Weissenborn-Luderode (DE); Olaf Kroll-Orywahl, Northeim (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 910 days.

(21) Appl. No.: 15/756,046

(22) PCT Filed: Aug. 30, 2016

(86) PCT No.: PCT/EP2016/070394
§ 371 (c)(1),
(2) Date: Feb. 27, 2018

(87) PCT Pub. No.: WO2017/037049
PCT Pub. Date: Mar. 9, 2017

(65) Prior Publication Data
US 2018/0250152 A1  Sep. 6, 2018

(30) Foreign Application Priority Data

Aug. 31, 2015 (DE) .......................... 102015114540.5

(51) Int. Cl.
*A61F 5/01* (2006.01)
(52) U.S. Cl.
CPC .......... *A61F 5/0123* (2013.01); *A61F 5/0102* (2013.01); *A61F 5/0125* (2013.01); *A61F 2005/0158* (2013.01); *A61F 2005/0165* (2013.01); *A61F 2005/0167* (2013.01)

(58) Field of Classification Search
CPC ...... A61F 2005/0158; A61F 2005/0165; A61F 2005/0167; A61F 5/0125; A61F 5/0123;
(Continued)

(56) References Cited

U.S. PATENT DOCUMENTS 3,833,942 A * 9/1974 Collins ................... A61F 2/582
623/60
4,711,241 A * 12/1987 Lehmann ............. A61L 17/145
427/2.31

(Continued)

FOREIGN PATENT DOCUMENTS

| CN | 201745635 U | 2/2011 |
|---|---|---|
| CN | 102574285 A | 7/2012 |

(Continued)

OTHER PUBLICATIONS

PCT International Search Report for PCT International Patent Application No. PCT/EP2016/070394, dated Nov. 16, 2016.

*Primary Examiner* — Michelle J Lee
*Assistant Examiner* — Robin Han
(74) *Attorney, Agent, or Firm* — Holland & Hart LLP

(57) ABSTRACT

A locking hinge with a first component and a second component which are mounted against each other in a pivotal manner relative to each other about a pivot axis. The first component has a latching recess, and the second component has a latching element which is designed to penetrate the latching recess in a latching position of the first component relative to the second component, thus preventing a pivoting movement of the first component relative to the second component in at least one direction. The latching element is designed to penetrate the latching recess to different depths in at least two different latching positions.

14 Claims, 7 Drawing Sheets

(58) Field of Classification Search
CPC ............ A61F 5/0102; A61F 2005/0132; A61F 2005/0139; A61F 2005/0144; A61F 2005/0146; A61F 2005/0134; A61F 2005/0137; A61F 2005/0141; A61F 2005/0148; A61F 2005/0151; A61F 2005/0153; A61F 2005/0155; A61F 2005/016; A61F 2005/0162; A61F 2005/0179; A61F 2002/6854; E05D 11/10; E05D 11/1007; E05D 11/1028; E05D 11/1035; E05D 11/105; E05D 11/1064; F16C 11/10
USPC ...... 602/16, 26; 16/319, 321, 324, 326, 327, 16/332, 349, 352
See application file for complete search history.

(56) References Cited

U.S. PATENT DOCUMENTS

| | | | |
|---|---|---|---|
| 4,711,242 A * | 12/1987 | Petrofsky | A61N 1/36003 602/26 |
| 5,885,235 A | 3/1999 | Opahle et al. | |
| 7,235,058 B2 * | 6/2007 | Doty | A61F 5/0123 602/26 |
| 8,920,060 B2 | 12/2014 | Maekita | |
| 2004/0225242 A1 | 11/2004 | Lidolt et al. | |
| 2005/0039762 A1 * | 2/2005 | Lidolt | A61F 5/0125 128/882 |
| 2005/0234376 A1 * | 10/2005 | Rossi | A61F 5/0193 602/16 |
| 2010/0262055 A1 * | 10/2010 | Schilling | A61F 5/0125 602/16 |

FOREIGN PATENT DOCUMENTS

| | | |
|---|---|---|
| CN | 203623762 U | 6/2014 |
| DE | 19606092 A1 | 8/1997 |
| DE | 19933197 A1 | 2/2001 |
| DE | 202006007451 U1 | 7/2006 |
| DE | 102007062961 A1 | 7/2009 |
| DE | 102007062961 B4 | 12/2012 |
| EP | 1457174 A2 | 9/2004 |
| EP | 1579829 A1 | 9/2005 |

* cited by examiner

LOCKING HINGE

TECHNICAL FIELD

The invention relates to a locking hinge, comprising a first component and a second component which are mounted on each other so as to be pivotable relative to each other about a pivot axis, wherein the first component has a locking recess and the second component has a locking element which is designed, in a locking position of the first component relative to the second component, to penetrate the locking recess and thus to prevent a pivoting movement of the first component relative to the second component in at least one direction. The invention also relates to an orthosis, in particular a knee orthosis, comprising a locking hinge of this type.

BACKGROUND

Locking hinges of this type are used in particular in orthopedics as hinges for orthoses, but may also be used in many other applications. If the locking hinge is used, for example, in a knee orthosis, the hinge is intended, for example in the swing phase of a step, to permit the extension, i.e. the stretching, of the knee joint. As soon as the knee has reached the full extension, i.e., for example, is stretched, the locking element penetrates the locking recess since the locking position of the two components with respect to each other has been reached. The effect achieved by this is that, when the foot is put down, pivoting of the two components relative to each other in the direction of flexion is blocked, and therefore the locking hinge can be loaded.

However, due to various causes, it is possible that, for example, the knee does not reach the required extension in a swing phase, since, for example, the patient is motor-impaired or, for example, stumbles. In this case, the locking element cannot penetrate the locking recess, and therefore a movement in the direction of flexion of the hinge cannot be blocked. If the leg and therefore the locking hinge in consequence are subjected to a load, pivoting of the two components relative to each other in the direction of flexion continues to be possible, and the support, anticipated by the patient, by means of the hinge fails to materialize and there is a threat of falling.

It is therefore known from DE 20 2006 007 451 U1 to arrange a functional element between the two components, said functional element having, over at least part of its circumference, a toothing in which the locking element engages. During pivoting of the two components relative to each other, for example during the extension or stretching of a knee joint, said pivoting movement is therefore not obstructed, while a movement in the opposite direction is prevented by the respective engagement of the locking element in the toothing on the outer side of the functional element. However, it is disadvantageous that, during each step and during each movement of the joint, the locking element slides away over the individual teeth of the toothing, and therefore said teeth are exposed to relatively severe wear. In addition, during each step, noises are produced if the locking element slides away over the individual teeth of the toothing and engages and drops into the intermediate spaces between adjacent teeth. Said noises may be perceived to be unpleasant and annoying.

SUMMARY

The invention is therefore based on the object of developing a locking element in such a manner that these disadvantages are eliminated.

The invention achieves the object which has been set by means of a locking hinge according to the preamble of claim 1, which is distinguished in that the locking element is designed to penetrate the locking recess to different depths in at least two different locking positions.

The effect achieved by this is that a plurality of locking positions are present, and therefore, even in the situation in which, for example, during pivoting of the joint, the final and definitively desired position, for example the extension stop, is not reached, pre-locking in a locking position located before said stop can take place. If the first component and the second component are therefore pivoted relative to each other about the common pivot axis, which can take place, for example, during the above-described extension of a knee joint, the two components reach a first of the various locking positions during said movement. At this time, the locking element penetrates the locking recess, and therefore, from this time, a pivoting movement of the two components in the opposite direction is no longer possible. In the above-described example of a knee orthosis, said first locking position is preferably reached before the definitive locking position, in particular the above-described extension stop, is reached. This gives rise to a safeguard which is of advantage in particular when the locking hinge is used in orthopedic devices, such as, for example, orthoses and in particular knee orthoses.

If the two components are pivoted further relative to each other in the original direction, i.e. if, for example, the locking hinge of the knee orthosis is moved further in the extension direction, the two components reach a second of the various locking positions at a later time. At this time, the locking element penetrates the locking recess to a greater depth, and therefore, from this moment, a pivoting movement in the opposite direction until the first locking position which was reached is also no longer possible. Said second locking position can be the definitively desired locking position, for example the extension stop. As an alternative thereto, of course, more than two different locking positions can also be reached. Since, in the process, a locking element does not, as in the prior art, slide away over a row of teeth, there is a significantly smaller degree of wear and virtually no production of noise.

In an advantageous manner, in order to penetrate the locking recess, the locking element moves in the radial direction with respect to the pivot axis. Said locking element particularly advantageously moves radially inward in order to be able to penetrate the locking recess. The locking element and/or the locking recess preferably have at least one step on at least one side surface. If the locking element has, for example, one step, said locking element will penetrate the locking recess as far as this step when the first locking position between the first component and the second component is reached. Further penetration is only possible, however, when the second locking position is reached and the locking element can penetrate further into the locking recess. There is analogous behavior if the locking recess has a corresponding step on one of its side surfaces. Of course, both the locking element and the locking recess can also have at least one step. Depending on the desired number of different locking positions, the locking element and/or the locking recess may also have a plurality of steps. The at least one step of the locking element preferably has a different width and/or a different depth than the at least one step of the locking recess. Of course, the steps of the locking element and/or the steps of the locking recess can also have widths and/or depths which differ from one another. A large number of locking positions which are optionally at different distances from one another can thereby be achieved by means of relatively simple manufacturing steps. Of course, equidistantly arranged locking positions can also be achieved in this manner.

In a preferred embodiment, the locking element and/or the locking recess has at least one side surface which is beveled relative to the radial direction. It has proven particularly advantageous if both the locking element and the locking recess each have a beveled side surface, wherein the two beveled side surfaces have the same angle relative to the radial direction. In this manner, the locking element, on exceeding the first locking position, penetrates continuously further into the locking recess, wherein the two beveled side surfaces of the locking element and of the locking recess slide on each other. Until the locking element has penetrated completely into the locking recess, that is if this is possible by means of the structural configuration, each position between the first component and the second component is consequently a locking position in which the locking hinge prevents a pivoting movement in the reverse direction.

In a preferred refinement of the invention, a pivoting angle about the pivot axis of between 0° and 30°, preferably between 5° and 15°, particularly preferably of 10°, lies between the two locking positions at the furthest distance from each other. Of course, however, other angular ranges are also possible depending on the desired application.

It has proven advantageous if the locking element is arranged in such a manner that, during the pivoting of the first component relative to the second component, said locking element slides along a surface of the first component, in which surface the locking recess is located. It has proven particularly advantageous if the locking element in this case is spring-loaded in the direction of the surface of the first component and, when a locking position is reached, is also spring-loaded in the direction of the locking recess. This ensures that the locking element securely slides into the locking recess and thus securely prevents a movement in the opposite pivoting direction.

At a later time, it may be entirely desirable for the locking hinge to be movable again in both directions and therefore for the first component to be pivotable relative to the second component in both directions about the pivot axis. For this purpose, the locking element has to be removed from the locking recess. It is therefore of advantage if the locking hinge has a release device which is designed to remove the locking element from the locking recess. Said release device can be designed in a wide variety of ways. For example, a mechanical or magnetic release device is conceivable. In particular in the case of a magnetically designed release device, there can be a solenoid which uses its magnetic force of attraction, which is controllable by the electric current, to draw the locking element out of the locking recess. As a result, a spring force which is optionally present and presses the locking element into the locking recess is overcome, and therefore, in this case, the first component is freely pivotable relative to the second component. The maximally possible pivoting movement is effected here if need be by means of structural stops or other configurations.

A mechanical release device can be actuated, for example, via a lever, a cable pull or a spring. In addition, pneumatic and/or hydraulic release devices are conceivable. By means of all of the release devices mentioned or other conceivable configurations of a release device, the locking element is drawn out of the locking recess and therefore the pivoting movement of the two components relative to each other is made possible again in both directions.

In addition, the invention achieves the object which has been set by means of an orthopedic device which has at least one locking hinge of the type described here. Use is advantageously made of two locking hinges which are arranged on different sides, for example medially and laterally, of a body part to which the orthosis is to be applied.

An orthopedic device can be, for example, an orthosis or a prosthesis. Such an orthosis or prosthesis can be used for an arm, a leg, a foot or a hand, and therefore the locking hinge described here or the locking hinges can be used for an elbow, a shoulder, a knee, a hip, an ankle or a wrist.

BRIEF DESCRIPTION OF THE DRAWINGS

An exemplary embodiment of the present invention is explained in more detail below with the aid of a drawing, in which.

DETAILED DESCRIPTION

Figure 1C:
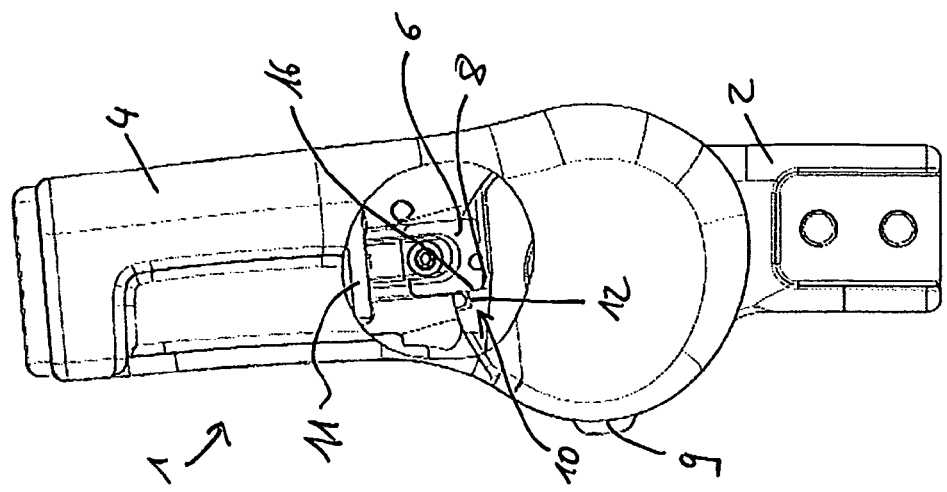
FIGS. 1a to 1c show the schematic illustration of a locking hinge in a partial sectional view.
Figure 1B:
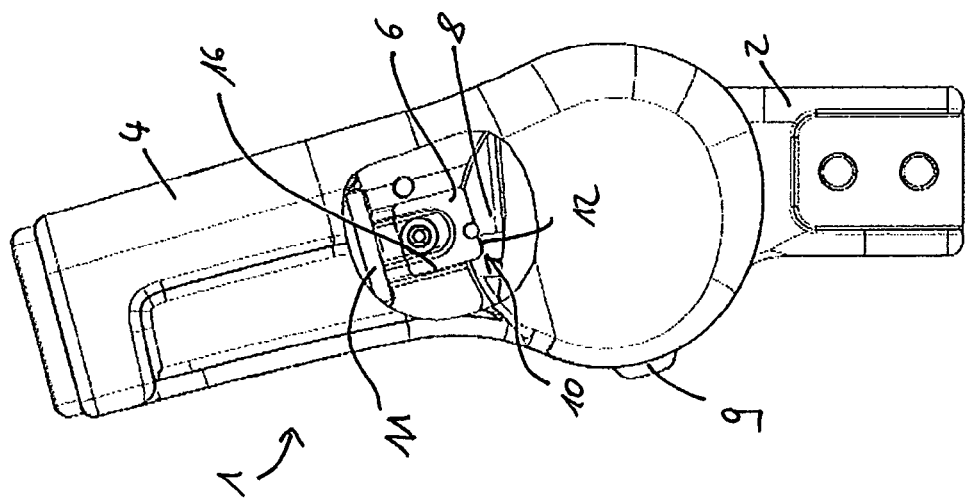
Figure 1A:
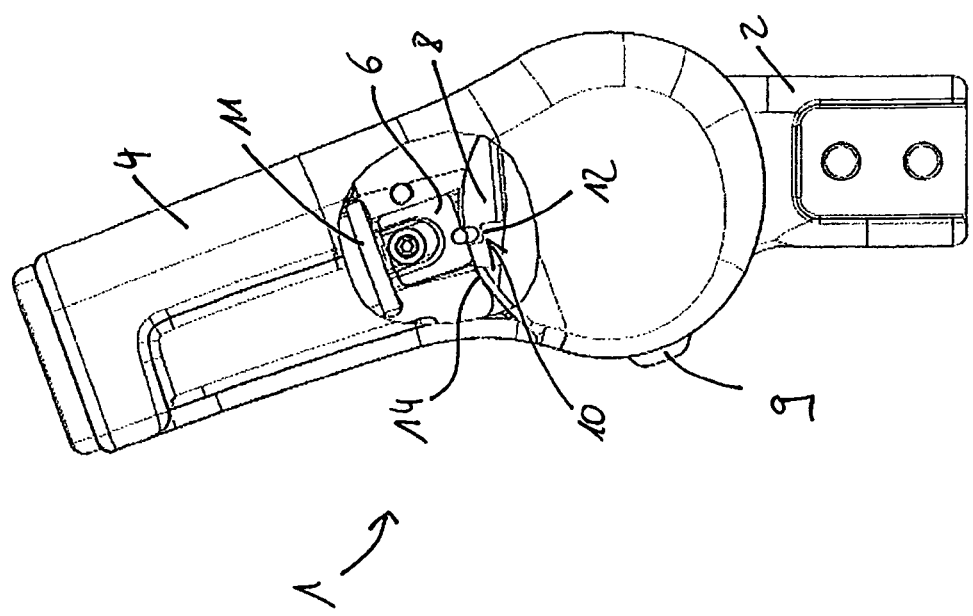

FIGS. 1a to 1c illustrate a locking hinge 1. Said locking hinge has a first component 2 and a second component 4. A locking element 6 is located on the second component 4, while the first component 2 has a locking recess 8. In FIGS. 1a to 1c, the first component 2 and the second component 4 are illustrated in three different positions relative to each other.

In FIGS. 1a to 1c, the locking recess 8 has a first side wall 10 which has a step 12 in FIGS. 1a to 1c.

In the situation shown in FIG. 1a, the locking element 6 lies against a surface 14 which is part of the first component 2. If the second component 4 is pivoted about a pivot axis (not illustrated in FIGS. 1a to 1c), the locking element 6 slides on said surface 14.

In FIG. 1b, the first component 2 and the second component 4 have reached the first locking position. It is seen that the locking element 6 has penetrated the locking recess 8 as far as the step 12. Further pivoting of the second component 4 relative to the first component 2 is possible only in the clockwise direction, but not in the opposite direction, since the locking element 6 lies with its second side wall 16 against the step 12 of the first side wall 10.

FIG. 1c shows the situation after the second locking position between the first component 2 and the second component 4 is reached. The locking element 6 has completely penetrated the locking recess 8 and now lies with its second side wall 16 against the lower part of the first side wall 10.

If the locking element 1 shown in FIGS. 1a to 1c is intended to be moved again in such a manner that the second component 4 can be rotated and pivoted counterclockwise relative to the first component 2, the locking element 6 has to be removed from the locking recess 8.

FIGS. 1a to 1c also illustrate a release device 11, by means of which the locking element 6 can be removed again from the position, shown in FIG. 1c, in the locking recess 8. In the exemplary embodiment shown, the release device 11 is designed as an electromagnetic release device 11, and therefore, by action thereupon with a current, a magnetic field can be produced, by means of which the locking element 6 can be removed from the position shown in FIG. 1c.

In addition, an emergency release 9 is illustrated, by means of which the locking hinge can always be released mechanically if this appears to be necessary.

Figure 2:
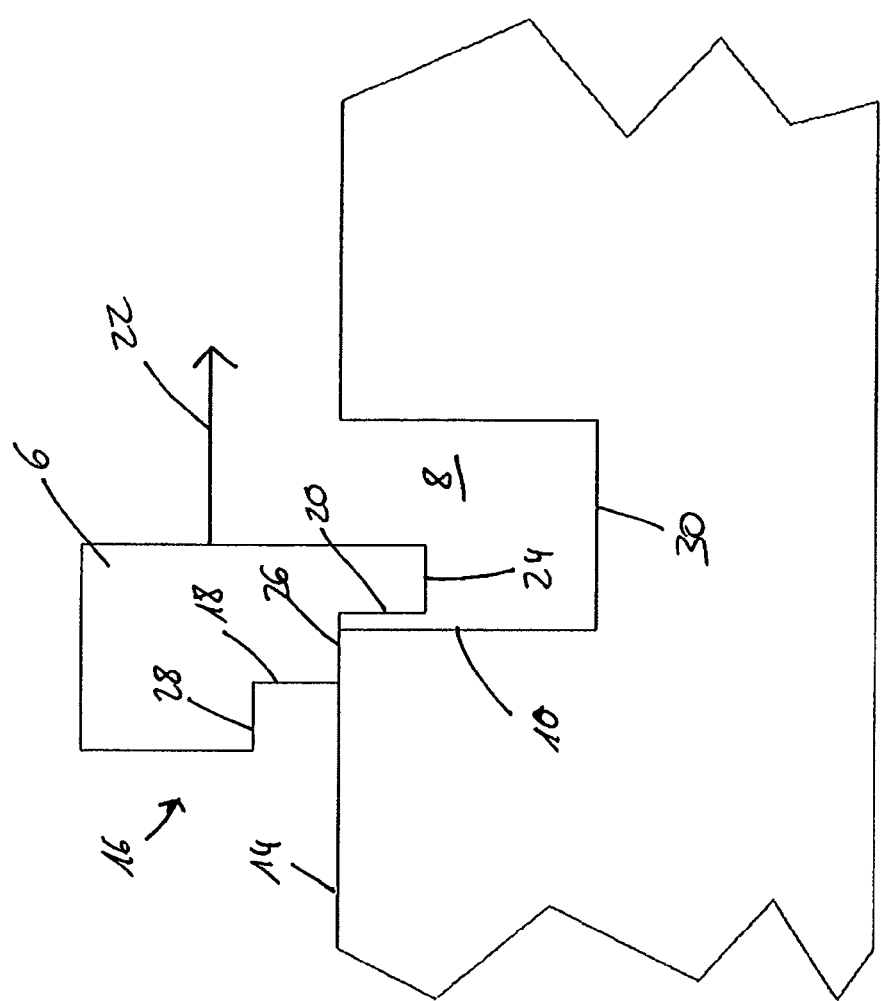
FIGS. 2 to 7d show different configurations of a locking recess and a locking element.

FIG. 2 shows the schematic illustration of part of a locking element 6 and of a locking recess 8. It is seen that the first side wall 10 does not have any structures whatsoever, but rather extends in the radial direction toward the pivot axis. The pivot axis is not illustrated in FIG. 2. The second side wall 16 of the locking element 6 has, by contrast, a first step 18 and a second step 20. If the first component 2 is now pivoted relative to the second component 4 in such a manner that the locking element 6 is moved in the direction of the arrow 22, first of all a lower side 24 of the locking element 6 will be arranged on the surface 14. In a certain position of the first component 2 relative to the second component 4, the first locking position is reached, and therefore the locking element can penetrate the locking recess 8 as far as the first step surface 26. This situation is illustrated in FIG. 2. If the locking element 6 is displaced further along the arrow 22, at a later time a second locking position is reached, in which the first step 18 can also penetrate the locking recess 8, wherein the locking element 8 penetrates the locking recess 8 until the second step surface 28 lies against the surface 14. Only at yet a later time is a third locking position reached, in which the locking element 6 can completely penetrate the locking recess 8 until the lower side 24 lies against a recess base 30 of the locking recess 8.

Figure 3:
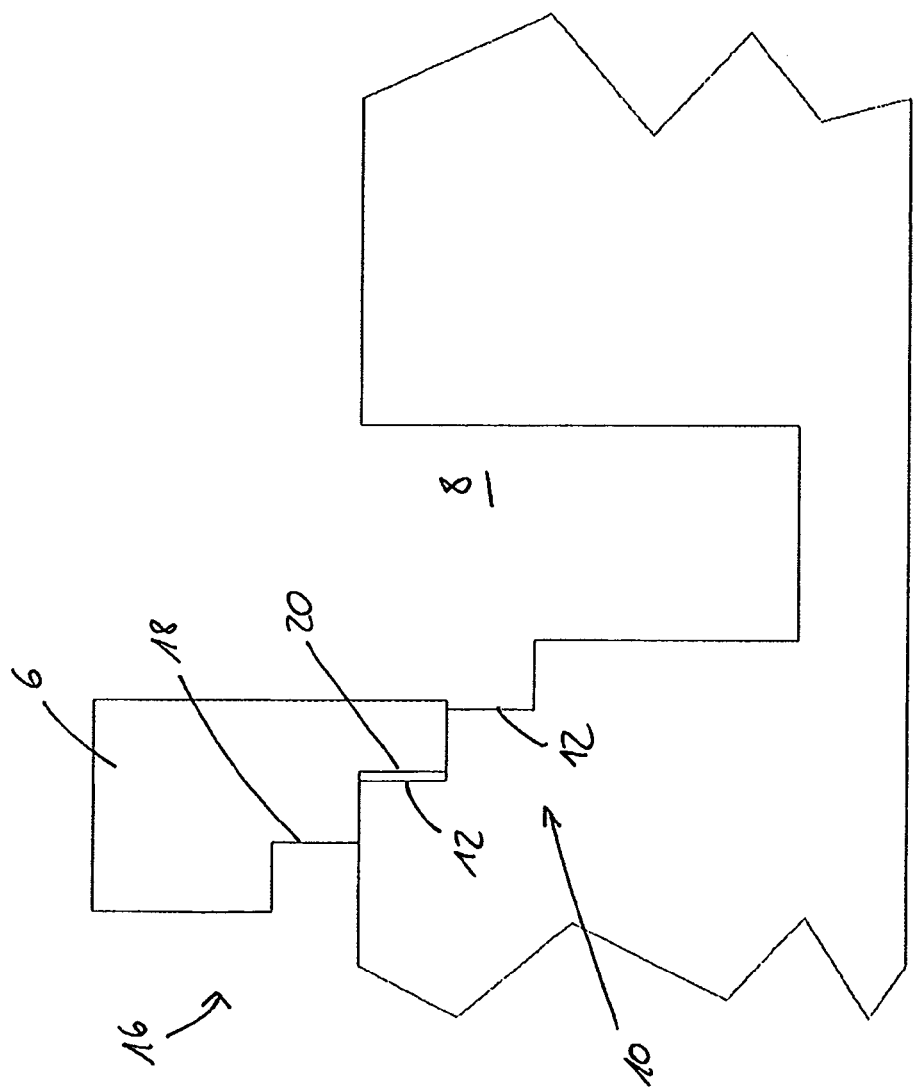

In FIG. 3, the second side wall 16 of the locking element 6 likewise has the first step 18 and the second step 20. However, in a different manner from the configuration shown in FIG. 2, the first side wall 10 of the locking recess 8 now also has two steps 12 which, in the exemplary embodiment shown in FIG. 3, have the same height and width as the first step 18 and the second step 20 of the locking element 6. While the embodiment of locking element 6 and locking recess 8 that is shown in FIG. 2 leads to three locking positions at an equidistant spacing from one another, the embodiment shown in FIG. 3 has five locking positions, in which the locking element 6 in each case penetrates further into the locking recess 8.

Figure 4:
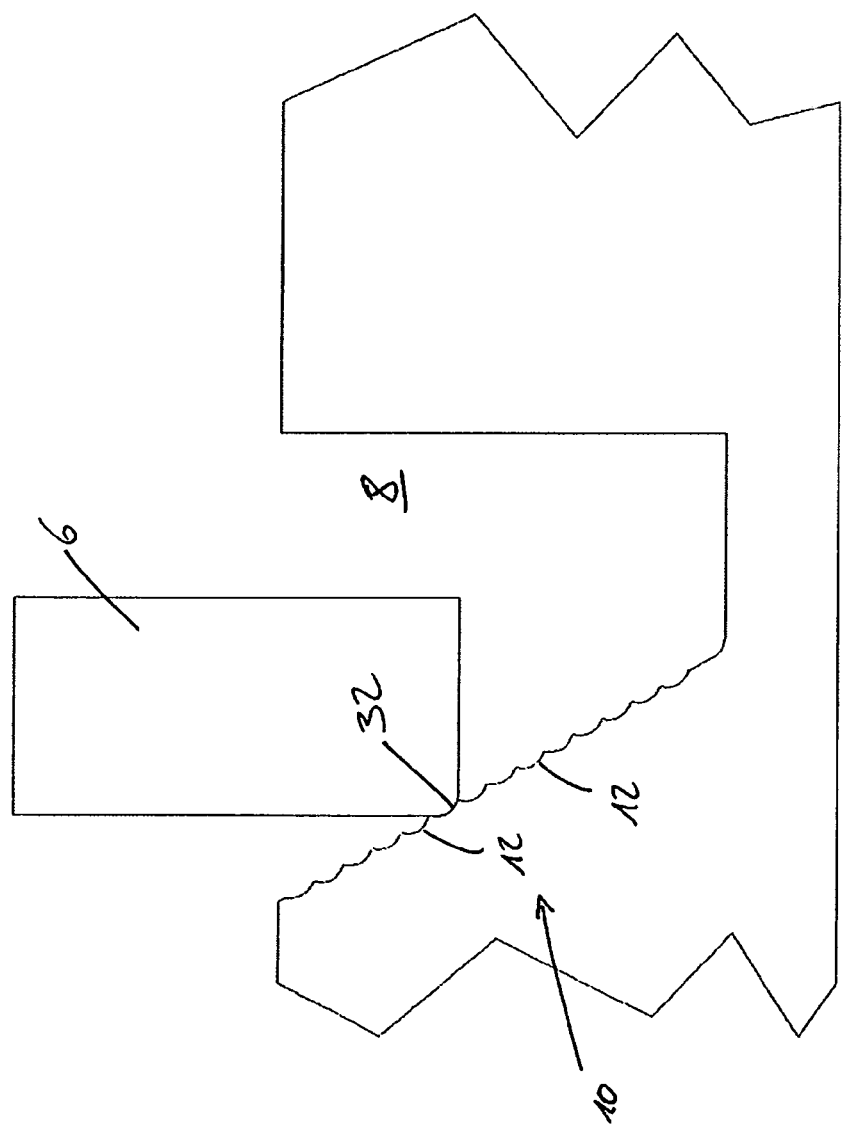

FIG. 4 shows a further configuration of a locking element 6 and a locking recess 8. The first side wall 10 of the locking recess 8 has a plurality of rounded steps 12, the contour of which corresponds to the contour of a rounded corner 32 of the locking element 6. If the locking element 6 in FIG. 4 is moved to the right, whenever the rounded corner 32 penetrates the next step 12 in each case, the locking element 6 will penetrate further into the locking recess 8, and therefore the next locking position in each case is always reached at these times.

Figure 5:
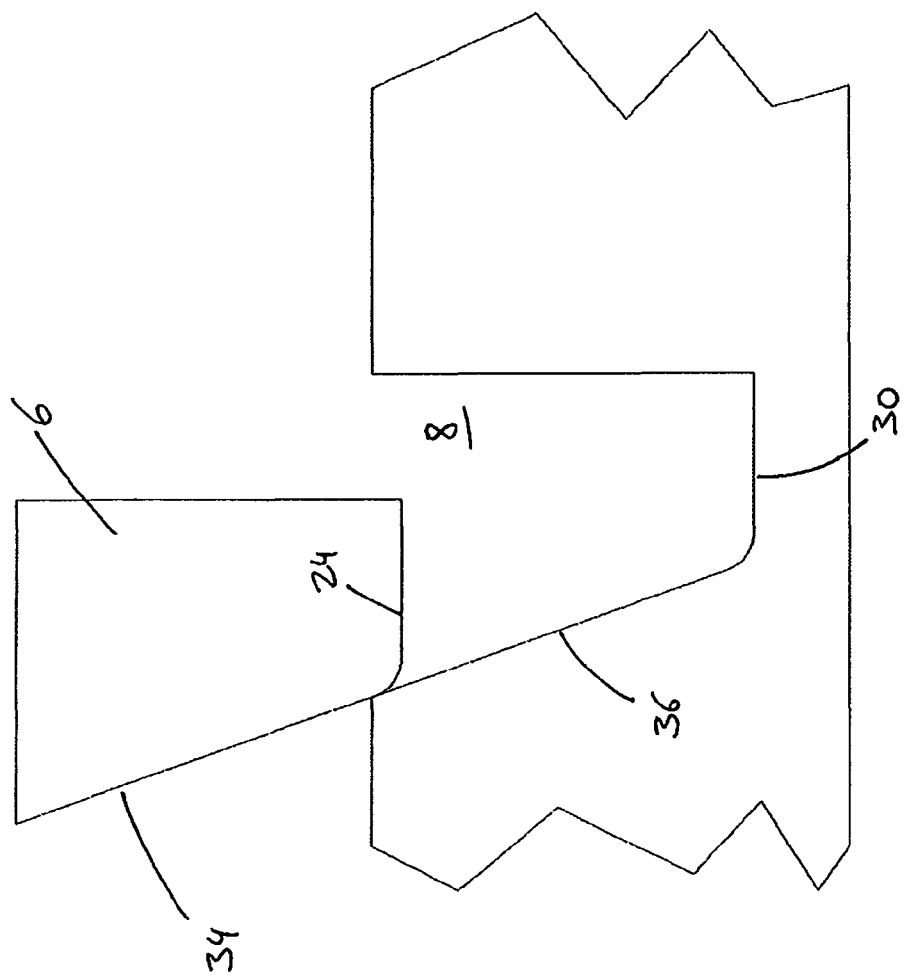

In FIG. 5, the first side wall 10 of the locking element 6 is designed as a beveled side surface 34. The second side wall 16 of the locking recess 8 is also designed as a beveled side surface 36, wherein it can readily be seen that the beveled side surfaces 34, 36 have the same angle relative to the radial direction, which extends downward in FIG. 5. The two beveled side surfaces 34, 36 can therefore slide on each other when the locking element 6 in FIG. 5 is moved to the right. The various locking positions are therefore distributed continuously until the locking element 6 is completely accommodated in the locking recess 8 and the lower side 24 lies against the recess base 30.

Figure 6B:
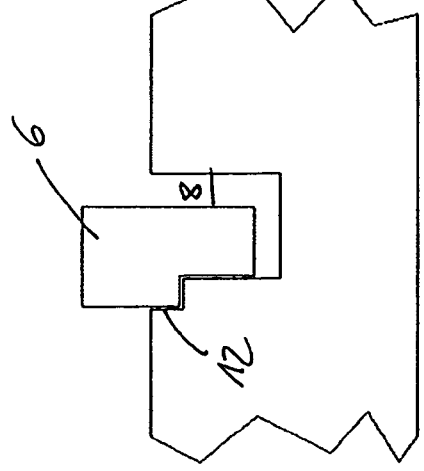
Figure 6A:
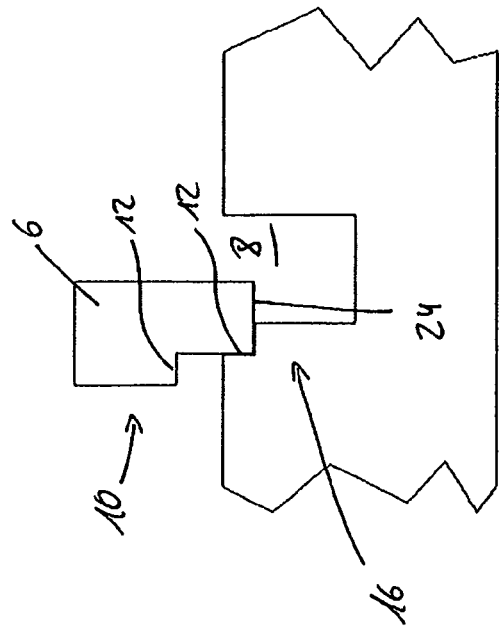
Figure 6C:
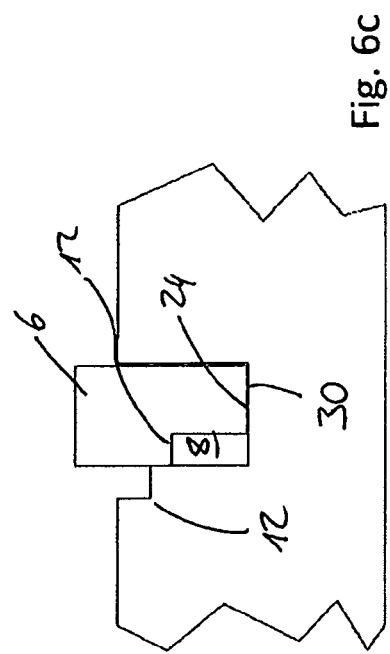
Figure 7A:
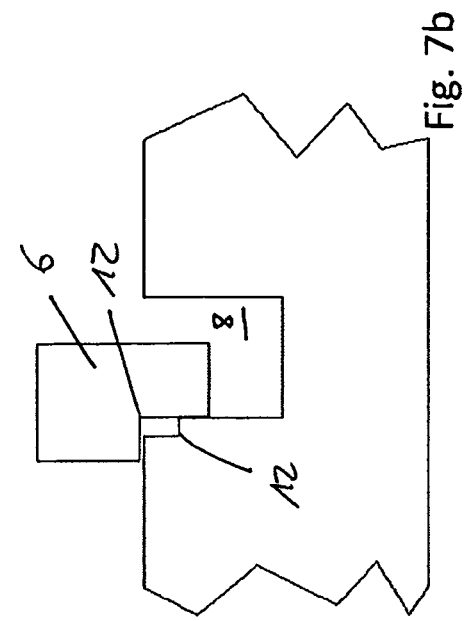
Figure 7B:
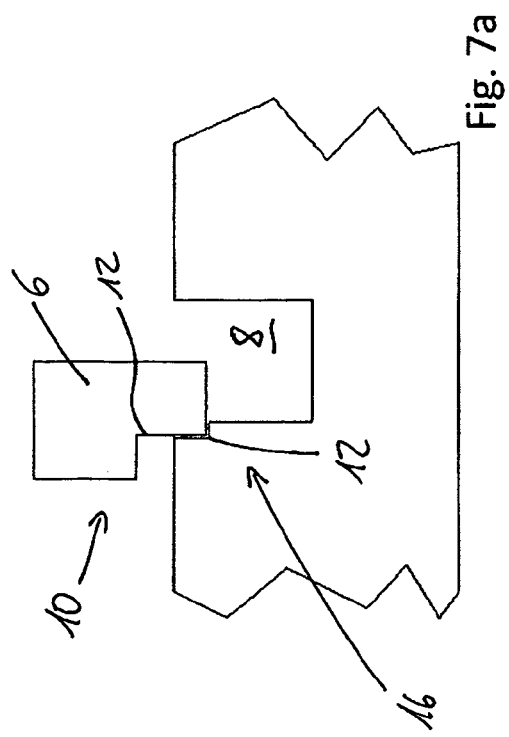
Figure 7C:
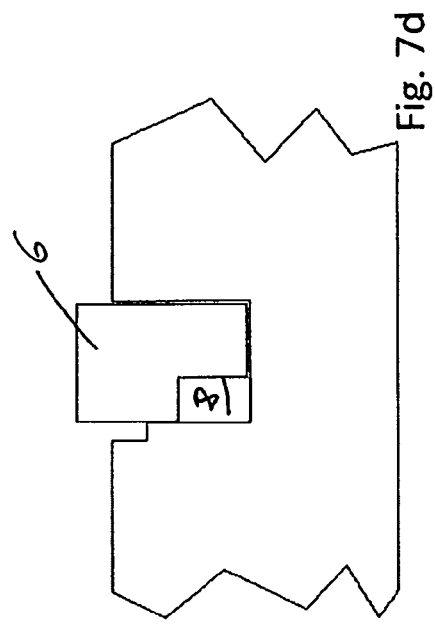
Figure 7D:
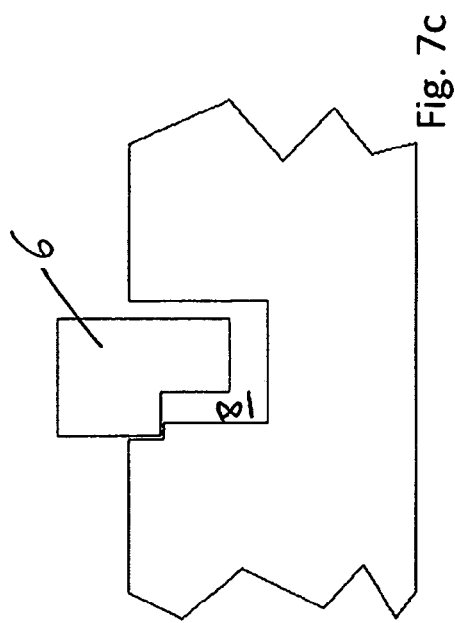

FIGS. 6a to 6c show various positions of the locking element 6 and of the locking recess 8. Both the first side wall 10 and the second side wall 16 each have a step 12, which steps can lie against each other in different positions. In FIG. 6a, this situation is illustrated when the first locking position is reached. The lower side 24 of the locking element 6 lies against the step 12 of the second side wall 16. In FIG. 6b, the locking element 6 has been displaced to the right relative to the locking recess 8, and therefore the two steps 12 here lie against each other. In FIG. 6c, the third and final locking position is reached by the locking element 6 having been displaced further to the right relative to the locking recess 8. The lower side 24 lies here against the recess base 30.

FIGS. 7a to 7d illustrate a further embodiment of the locking element 6 and of the locking recess 8.

It is seen that both the first side wall 10 of the locking element 6 and the second side wall 16 of the locking recess 8 have a respective step 12, which steps, however, differ in width in the exemplary embodiment shown. In FIGS. 7a to 7d, the locking element 6 is displaced ever further to the right relative to the locking recess 8, and therefore said locking element can penetrate to ever greater depth into the locking recess 8. By means of the different width of the steps, which also have a different height, the four locking positions shown in FIGS. 7a to 7d are made possible, wherein the locking element 6 penetrates into the locking recess 8 to an ever greater depth as it is progressively displaced to the right relative to the locking recess 8.

This configuration has the advantage that a relatively large number of different locking positions can be achieved and realized in a manner which can be produced particularly simply, and therefore the outlay on manufacturing is low and the additional security achieved for the locking hinge is high.

LIST OF REFERENCE SIGNS 1 locking hinge
2 first component
4 second component
6 locking element
8 locking recess
9 emergency release
10 first side wall
11 release device
12 step
14 surface
16 second side wall
18 first step
20 second step
22 arrow
24 lower side
26 first step surface
28 second step surface
30 recess base
32 rounded corner
34 beveled side surface
36 beveled side surface

The invention claimed is:

1. A locking hinge, comprising: a first component and a second component, which are mounted on each other so as to be pivotable relative to each other about a pivot axis, the first component having a single locking recess and the second component having a locking element; wherein the locking element is configured to automatically penetrate the locking recess to a first depth within the single locking recess upon the first component reaching a first rotation position relative to the second component, and wherein the locking element is configured to automatically penetrate the locking recess to a second depth within the single locking recess upon the first component reaching a second rotation position relative to the second component, the first and second positions and the first and second depths representing at least two locking positions that prevent pivoting movement of the first component relative to the second component in a first direction and permit pivoting movement of the first component relative to the second component in a second direction opposite the first direction, wherein the second depth is deeper within the locking recess than the first depth, wherein at least one of the locking element and the locking recess have a first step corresponding to the first depth, and a second step corresponding to the second depth.

2. The locking hinge as claimed in claim 1, wherein a pivoting angle about the pivot axis of between 0° and 30° lies between the two locking positions at a furthest distance from each other.

3. The locking hinge as claimed in claim 2, wherein the pivoting angle is between 5° and 15°.

4. The locking hinge as claimed in claim 1, wherein, in order to penetrate the locking recess, the locking element moves in a radial direction with respect to the pivot axis.

5. The locking hinge as claimed in claim 1, wherein the first step and second step of the locking element and the first step and second step of the locking recess are designed to at least one of differ in width and differ in depth.

6. The locking hinge as claimed in claim 1, wherein the locking element is arranged in such a manner that, during pivoting of the first component relative to the second component, the locking element slides along a surface of the first component in which the locking recess is located.

7. The locking hinge as claimed in claim 1, further comprising a release device which is designed to remove the locking element from the locking recess.

8. An orthopedic device, comprising at least one locking hinge as claimed in claim 1.

9. A locking hinge, comprising: a first component having a single locking recess; and a second component pivotally mounted to the first component about a pivot axis, the second component having a locking element, the locking element configured to automatically extend into the single locking recess to a first depth within the single locking recess upon the first component reaching a first rotation position relative to the second component, and wherein the locking element is configured to automatically penetrate the locking recess to a second depth within the single locking recess upon the first component reaching a second rotation position relative to the second component, the first and second positions and the first and second depths representing at least two different locking positions to prevent pivoting movement of the first component relative to the second component in a first direction and permit pivoting movement of the first component relative to the second component in a second direction opposite the first direction, wherein the second depth is deeper within the locking recess than the first depth, wherein the locking element and the locking recess each have a first step corresponding to the first depth, and a second step corresponding to the second depth.

10. The locking hinge as claimed in claim 9, wherein the locking element moves in a radial direction with respect to the pivot axis in order to extend into the locking recess.

11. The locking hinge as claimed in claim 9, wherein the first step and the second step of the locking element and the first step and second step of the locking recess differ in at least one of width and depth.

12. The locking hinge as claimed in claim 9, wherein a pivoting angle about the pivot axis of between 0° and 30° lies between the two locking positions at a furthest distance from each other.

13. The locking hinge as claimed in claim 9, wherein the locking element is arranged in such a manner that the locking element slides along a surface of the first component in which the locking recess is located during pivoting of the first component relative to the second component.

14. The locking hinge as claimed in claim 9, further comprising a release device which is designed to remove the locking element from the locking recess.

\* \* \* \* \*